(12) United States Patent
Cowburn et al.

(10) Patent No.: US 8,146,403 B2
(45) Date of Patent: Apr. 3, 2012

(54) GAS SENSOR WITH SMART PELLISTOR

(75) Inventors: Anthony R. Cowburn, Eastleigh (GB);
David F. Davies, Southampton (GB);
Jonathan H. Gilby, Chichester (GB)

(73) Assignee: Life Safety Distribution AG, Uster (CH)

( * ) Notice: Subject to any disclaimer, the term of this patent is extended or adjusted under 35 U.S.C. 154(b) by 374 days.

(21) Appl. No.: 12/209,086

(22) Filed: Sep. 11, 2008

(65) Prior Publication Data
US 2009/0223278 A1 Sep. 10, 2009

Related U.S. Application Data

(60) Provisional application No. 60/972,844, filed on Sep. 17, 2007.

(51) Int. Cl.
*G01N 19/10* (2006.01)
(52) U.S. Cl. .................. 73/23.2; 73/23.31; 73/25.01
(58) Field of Classification Search .................. 73/23.2, 73/23.31, 25.01
See application file for complete search history.

(56) References Cited

U.S. PATENT DOCUMENTS

| | | | |
|---|---|---|---|
| 2,099,548 A | 11/1937 | Vayda et al. | |
| 4,817,414 A | 4/1989 | Hagen et al. | |
| 5,070,732 A | 12/1991 | Duncan et al. | |
| 5,142,898 A | 9/1992 | Kauschke et al. | |
| 5,526,280 A | 6/1996 | Consadori et al. | |
| 5,601,693 A | 2/1997 | Davies | |
| 6,053,031 A | 4/2000 | Kullik et al. | |
| 6,442,994 B1 * | 9/2002 | Slater | 73/23.31 |
| 6,687,005 B2 | 2/2004 | Kim | |
| 6,911,180 B2 | 6/2005 | Miller et al. | |
| 6,954,702 B2 | 10/2005 | Pierry et al. | |
| 7,193,406 B2 | 3/2007 | Mori et al. | |
| 7,244,939 B2 * | 7/2007 | Stuttard | 250/343 |
| 7,287,414 B2 | 10/2007 | Bahs et al. | |
| 2003/0019747 A1 | 1/2003 | Saffell et al. | |
| 2003/0190262 A1 | 10/2003 | Blazewicz et al. | |
| 2005/0280408 A1 | 12/2005 | Wobschall | |
| 2006/0032745 A1 * | 2/2006 | Davies et al. | 204/431 |
| 2007/0274868 A1 | 11/2007 | Brown | |

FOREIGN PATENT DOCUMENTS

| | | |
|---|---|---|
| EP | 0 252 283 | 1/1988 |
| GB | 2 326 239 A | 12/1998 |
| KR | 20010050997 | 8/2001 |
| WO | WO9106849 | 5/1991 |
| WO | WO 9530144 | 11/1995 |
| WO | WO2005015176 | 2/2005 |

(Continued)

OTHER PUBLICATIONS

Product Data Sheet: IRceL CO2, http://www.citytech.com/PDF-Datasheets/ircelco2.pdf, Ircelco2 Rev 01, Issue 2, ECN, Apr. 3, 2007.

(Continued)

*Primary Examiner* — Hezron E Williams
*Assistant Examiner* — Rodney T Frank
(74) *Attorney, Agent, or Firm* — Husch Blackwell

(57) ABSTRACT

A gas sensor includes a gas responsive pellistor and associated information specific to that pellistor. The information can include environmental compensation information, such as temperature or humidity compensation information or other manufacturing information, and is stored in a computer readable medium. Such information can be used by local circuitry in compensating the sensor while making ambient gas level determinations.

21 Claims, 3 Drawing Sheets

FOREIGN PATENT DOCUMENTS

WO  WO 2005/054827 A1  6/2005

OTHER PUBLICATIONS

Product Data Sheet: IRceL CH4, http://www.citytech.com/PDF-Datasheets/ircelch4.pdf, Ircelch4 Rev 01, Issue 2, ECN, Apr. 3, 2007.

City Technology: Pellistors, http://www.citytech.com/technology/pellistors.asp, Oct. 21, 2007.

http://www.citytech.com/images/diagrams/ir-fig2.gif, Oct. 21, 2007.

\* cited by examiner

GAS SENSOR WITH SMART PELLISTOR

CROSS-REFERENCE TO RELATED APPLICATION

This application claims the benefit of the filing date of U.S. Provisional Application Ser. No. 60/972,844 filed Sep. 17, 2007 and entitled "Smart Pellistor". The '844 application is hereby incorporated herein by reference.

FIELD

The invention pertains to pellistor based sensors that are designed to provide a measure of % LEL of combustible gases. More particularly, the invention pertains to such sensors which incorporate temperature compensating information.

BACKGROUND

Gas responsive sensors, implemented by pellistors are known. Embodiments of such sensors are disclosed in U.S. Pat. No. 5,601,693 which issued Feb. 11, 1997, entitled Gas Sensor. The '693 patent is incorporated herein by reference.

The accuracy of a gas sensor is important in terms of both span/sensitivity, and baseline stability. The baseline can be affected by the ambient temperature, particularly for devices that do not have pellistors, or beads, on open headers. Such devices might have shock absorbing glass wool in close proximity to the beads. This structure can influence the thermal performance to a greater degree than beads that are mounted 'in the open', on headers.

As a result of such thermal effects different individual sensors may experience a baseline offset, either positive or negative, when subjected to an ambient thermal shift (e.g. from +20 C to −20 C). The thermal shift can be compensated by the instrument, and in general instruments use an average thermal shift figure for a given product (established empirically, as an average of the population).

The bead manufacturing process aims to make both beads a consistent size (and therefore thermal mass/performance), such that both detector and compensator respond in a similar way to changes in ambient temperature. However, these thermal offsets can vary from one sensor to another if the 'thermal match' between the detector and compensator beads is not ideal, and this can lead to significant errors.

In order to achieve greater accuracy in extreme temperature environments such sensors can be screened to eliminate the extremes in the temperature profile. The limits set for an ambient temperature shift from +20 C to −20 C are baseline shifts of up to −6% LEL to +3.5% LEL. With the screen in place the customer knows that the instrument will not give false readings outside of this acceptable zone when making 40 C ambient temperature changes. The actual thermal performance range for the existing products (City 4P90, 4P75 and MICROpeL 75) is about −10% LEL to +6% LEL. Screening to the −6% LEL to +3.5% LEL limits results in a process capability of about Cpk 0.7, and is expected to create a fallout/scrap rate of between 6% and 15% of the product.

There is a need to be able to address these thermal effects more efficiently than has been possible with known sensors. It would be desirable to provide individualized compensation for each sensor both at initial manufacture and subsequently in the replacement market to provide the most accurate gas detection possible.

DETAILED DESCRIPTION

Figure 1:
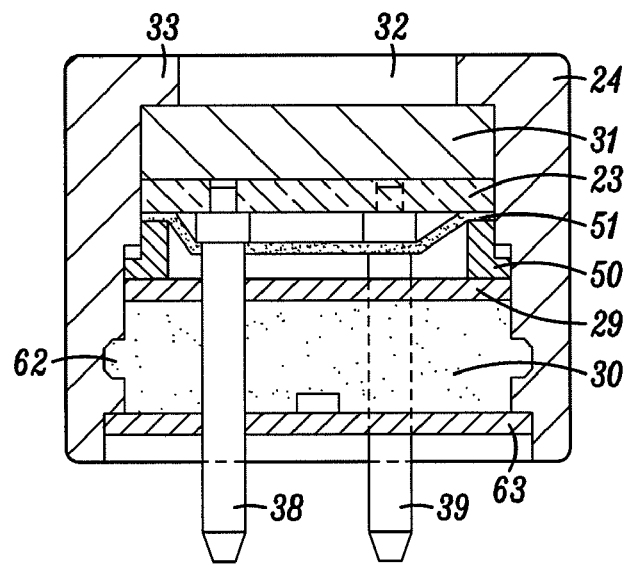
FIG. 1 is a section through a gas sensor according to the present invention.

While embodiments of this invention can take many different forms, specific embodiments thereof are shown in the drawings and will be described herein in detail with the understanding that the present disclosure is to be considered as an exemplification of the principles of the invention, as well as the best mode of practicing same, and is not intended to limit the invention to the specific embodiment illustrated.

Embodiments of this invention store the measured thermal offset data for individual sensors in a way that links it directly with that individual sensor, such that the individual offset can be easily factored into the instrument during build to allow accurate, individual compensation. The baseline thermal offset with ambient temperature changes will then be individually compensated, resulting in improved accuracy in the instrument along with improved yield, costs and robustness of the sensor manufacturing process.

There are several different embodiments.

1st—EEPROM within sensor (Preferred).

This first method involves the use of an EEPROM within the pellistor housing. The EEPROM is designed such that data can be up or down loaded via an existing connection pin. Other types of storage circuits come within the spirit and scope of the invention.

Figure 5:
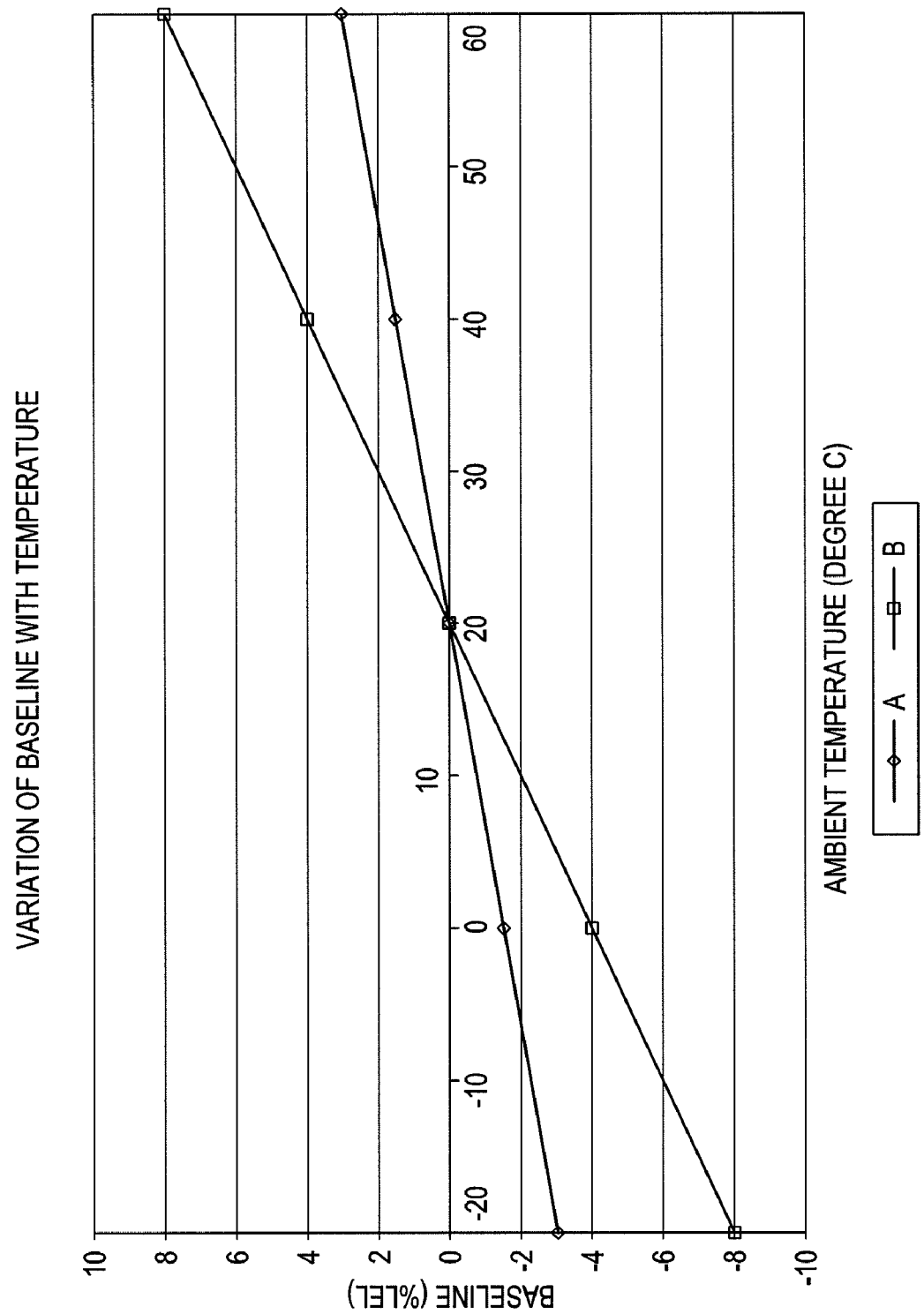
FIG. 5 is an exemplary graph of baseline variation of two different sensors as a function of temperature.

The thermal performance data, as illustrated in FIG. 5 for two different sensors, gathered during a +20 C to −20 C screen test is assessed and can be converted to a compensation factor, then written to the EEPROM in the respective sensor. The sensor is subsequently inserted into a detector, or instrument. The detector can be configured to download the EEPROM data on power-up, such that the exact thermal compensation for that individual sensor can be used in the detector in order to eliminate most ambient temperature effects.

Anticipated advantages:

A) It is envisaged that a performance far better that the −6% LEL to +3.5% LEL specification could be achieved in the instrument.

B) There would be no need to reject any sensors at the extremes of the thermal profile as all could be individually compensated—thus eliminating the expected 6% to 15% yield fallout (for currently manufactured pellistors).

C) Eliminate need for very tight process control in pellistor manufacturing process.

2nd—2 dimensional barcode version.

A second option is to encode the thermal compensation data into the 2D barcode, such that the information could be scanned into the detector during manufacture.

An aspect of this embodiment is that sensor replacement in the field would require use of selected units. Field replacement sensors would need to be selected to be from the centre of the population, and the instrument configured to implement a nominal average figure for the thermal compensation of a replacement sensor.

3rd—a database version.

A third option is to pull the thermal compensation data from a database during manufacturing of the detector, or, instrument. The thermal offset data will be available for each sensor serial number, so the individual thermal offset could be loaded into the instrument based on sensor serial number and access to the database.

Some of the same considerations apply to this system as are applicable to the 2D barcode version. Field replacement sensors could be selected to be from the centre of the population, and the instrument configured to implement a nominal average figure for the thermal compensation of a replacement sensor.

A sensor which embodies the invention is, in one embodiment, designed to detect a build up of potentially explosive atmospheres as occasionally happens in coal mines and oil rigs. Fortunately, such build ups do not occur too often so that the sensor spends most of its working life sitting in "air" and reading "zero".

This air reading is referred to as the "baseline reading". One characteristic of such sensors is that this baseline reading changes as a result of changes in ambient temperature. As a result, a sensor can be reading "zero" when in a centrally heated office at around 20 degree C., but shows a significantly different value when taken outdoors into a −30 degree C. temperature. It is undesirable to have a sensor (installed in a detector, or instrument) suddenly changing its indication from 0% LEL to (say) minus 8% LEL simply because an individual carrying or wearing the detector walked out the door from a relatively warm environment to a much colder environment.

A further aspect is that the magnitude of this baseline change with temperature (or baseline shift) differs from sensor to sensor. Some sensors show a small baseline shift and are acceptable whereas others shift by greater amounts and are unusable. One way to separate the good from the bad is to actually measure the baseline shift by subjecting the sensor to a change in temperature in some form of test chamber.

The baseline shift can be measured for each sensor. Those sensors that don't meet a certain pre-ordained performance can then be rejected. In the graph of FIG. 5, Sensor A would be regarded as acceptable but Sensor B would be rejected. The baseline shift for Sensor B on going from 20 degree C. to −20 degree C. (−8% in the graph) is regarded as too great.

In accordance with the invention, by relating each sensor to its own temperature data, sensors could be individually compensated in an instrument with a combination of electronics/software. Sensors that would now be rejected (Sensor B for example), when embedded with their own, unique, temperature data, could be incorporated in detectors, or, instruments capable of reading the embedded data and making the necessary adjustments in the event of any ambient temperature change. Both instrument performance and yield in sensor production would be improved.

Figure 2:
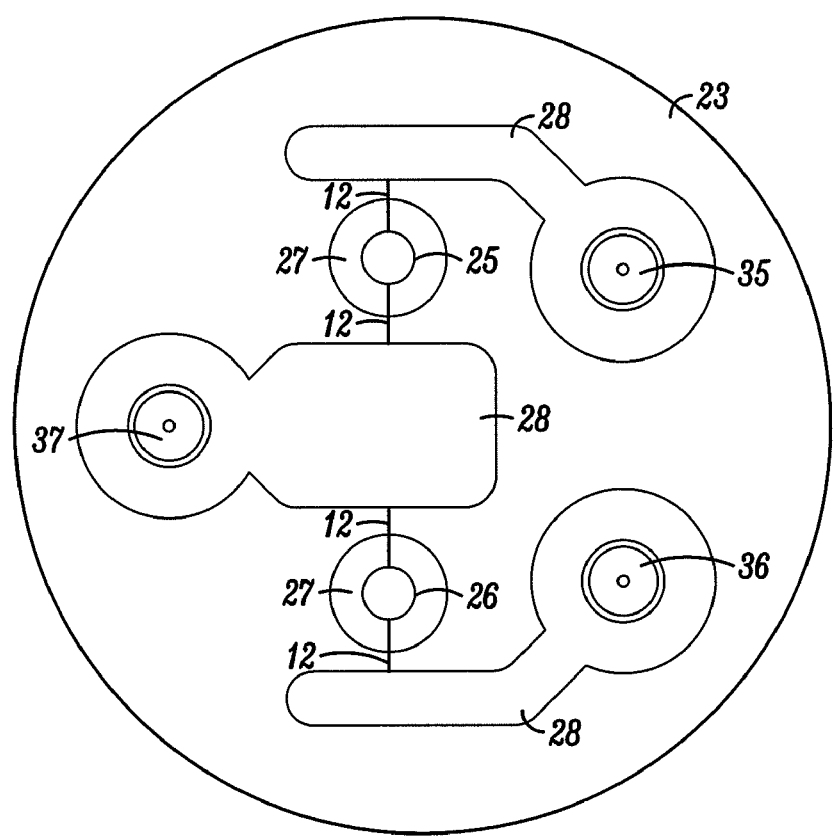
FIG. 2 is a plan view of the substrate of the device as shown in FIG. 1.

One example of a sensor according to the present invention is shown in FIGS. 1 and 2. A ceramic substrate 23 or other substrate, for example a printed circuit board, is mounted in a housing 24, typically made of stainless steel. The ceramic substrate 23 supports a pair of gas sensing elements, a compensator element 25 and a detector element 26. The gas sensing elements have a similar construction to those described above. The elements are, in this embodiment, mounted within openings 27 in the substrate 23. Leads 12 from the elements 25,26 are connected (surface mounted) to electrical tracks 28 on a surface of the substrate 23 as shown in FIG. 5 using conducting cement or by welding etc.

The substrate 23 is clamped against a sinter layer 31 in the housing 24 by means of a compression ring 50. The compression ring 50 also serves to retain a layer 51 of inert, insulating material such as glass or ceramic wool in position between the beads 25, 26 and a separating layer 29. The layer 51 essentially removes the effect of changes in orientation on the sensor by substantially preventing convection currents and improves the shock resistance of the device. Similar material could also be provided in the apertures 27 on the sinter layer side. The separating member 29 is provided to separate and protect the elements 25, 26 and the layer 51 from a layer of potting compound 30. The separating member 29 may be a printed circuit board, or a ceramic or plastic cover. A groove 62 is provided around the inner surface of the housing 24 so that the potting compound can be provided with a key.

Three connectors, two of which 38, 39 are shown in FIG. 1, extend upwardly from the tracks 28 at 35-37. These connectors provide electrical connections to the measurement or monitoring circuitry which is to be described below.

The rear closing plate 63 is mounted to the housing 24 on the other side of the potting compound 30. The underside of the rear closing plate 63 is shown in more detail in FIG. 9. The plate 63 is in the form of a printed circuit board having three apertures 64-66 through which the connectors 38-40 respectively extend. Surrounding these apertures 64-66 are respective metallic conducting regions 67-69 to which the respective connectors 38-40 are soldered. In addition, the metallic conducting regions 66, 67 are coupled via tracks 70 to a trimming resistor 71. The rear closing plate 63 also has two apertures 72 through which potting compound can be supplied.

An opening 32 defined by a flange 33 of the housing 24 allows a gas being monitored into the device whilst still affording adequate protection to the sinter layer 31.

Each element 25, 26 may be manufactured on a conventional base so that the construction problems of keeping the substrate free of ceramic and catalyst do not have to be taken into account. The element is then surface mounted to the substrate 23 as described above with an adequate clearance around the bead.

Alternatively, the opening 27 in the substrate 23 is arranged to give sufficient clearance to build up a bead over a coil in situ.

Figure 3:
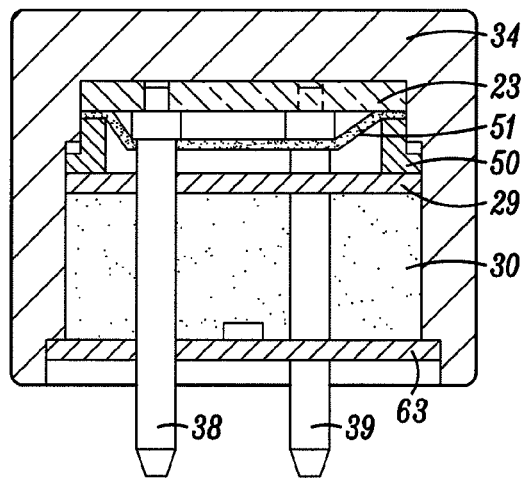
FIG. 3 is a gas sensor according to the present invention with an alternative housing arrangement.

An alternative arrangement is shown in FIG. 3. The substrate 23 is mounted in a housing 34 with the separating member 29 and the glass wool layer 51 above the elements 25, 26 to separate them from the potting compound 30 which is covered by a rear closing plate 63. However, in this case, there is no separate sinter layer. Instead the housing 34 is formed of sinter throughout. This allows the overall thickness to be further reduced.

Figure 4:
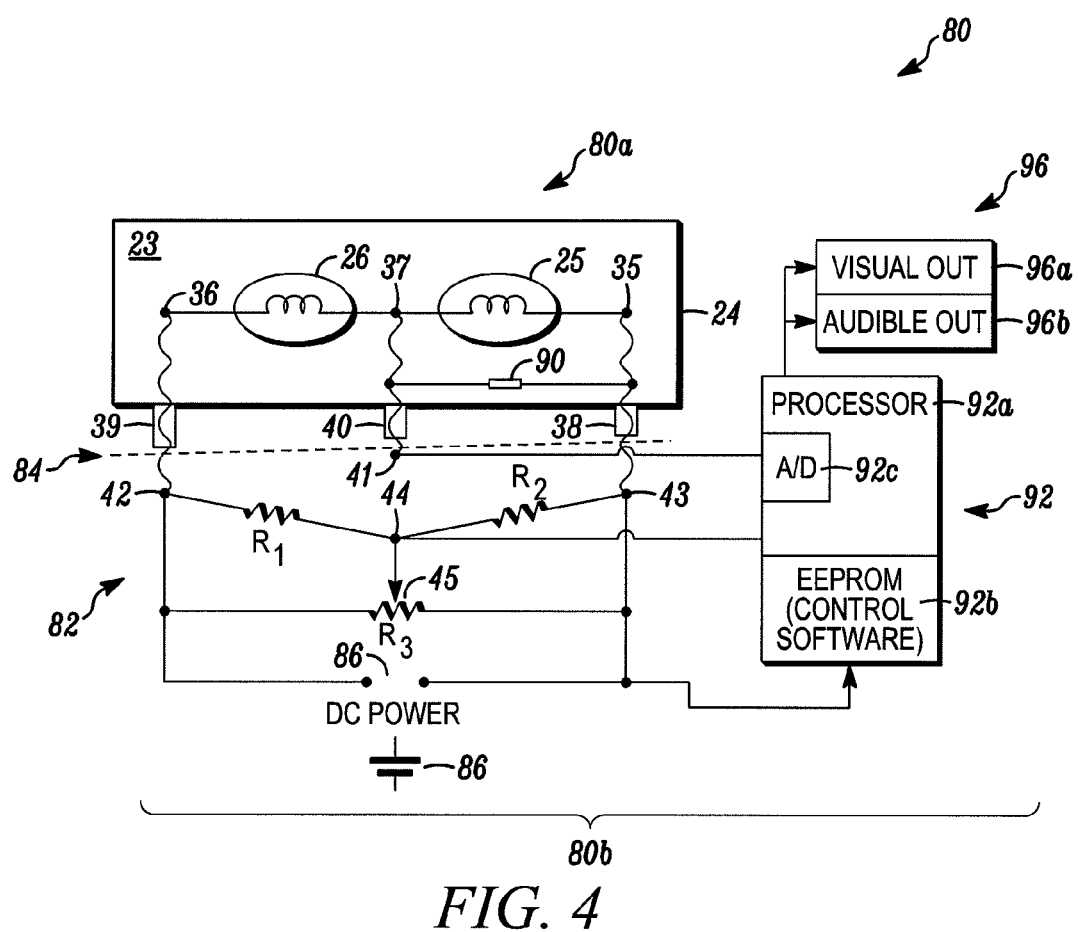
FIG. 4 is a circuit diagram of a detector which includes a sensor as in FIG. 1 or 3.

FIG. 4 is a circuit diagram illustrating a detector 80 which includes a sensor 80a such as in FIG. 1 or 3. Either of the sensors shown in FIGS. 1 to 3 can be coupled to a Wheatstone bridge 82. As can be seen in FIG. 4, the connectors 38-40 extending from the tracks at 35-37 extend out of the container 24 and can slidably, and replacably, engage a socket 84 of detector 80.

The connector 40 forms one output point 41 directly while the connectors 39, 38 are coupled to respective resistors $R_1$, $R_2$ at 42, 43 respectively. The resistors $R_1$, $R_2$ are connected at 44 to a zero set variable resistor 45 which can be adjusted between 0 and 1 kohm. The point 44 constitutes the other output pole. DC power is supplied from a source 86, for example a battery, to the two points 42, 43. The resistors $R_1$, $R_2$ would each typically be fixed at 27 ohm although in some cases these could be varied.

A storage circuit 90, for example a read-only memory circuit, or an electrically erasable programmable read only memory, EEPROM, can be coupled between the connectors 38, 40. Circuit 90 can be loaded with temperature compensation information specific to the elements 25, 26 of sensor 80a and is provided to compensate for differences in performance, as illustrated in FIG. 5, of the elements 25, 26 with temperature.

Sensor 80a can be coupled via 41, 44 to control circuits 92 carried in housing 80b. Circuits 92 can be implemented as a programmable processor 92a, associated, pre-stored control circuits 92b and an analog/digital converter 92c. Control circuits 92 can determine, based on signals from sensor 80a, in conjunction with a temperature compensation factor obtained from storage circuitry 90, a level of gas concentration, expressible for example as a % LEL for a selected gas. Control circuits 92, can provide gas concentration information in visual or audible form via output devices 96.

The compensator element 25 and gas detector element 26 could alternately be coupled in parallel. In other embodiments, only the detector element 26 need be used. Additionally, information as to a humidity coefficient could be stored in storage element 90 alone or in combination with the above described temperature compensating information. Other environmental information or, manufacturing information could also be stored in element 90 for subsequent use.

It will be understood that if sensor 80a is replaced for any reason, the replacement unit will also include a storage circuit, comparable to circuit 90, which can be accessed and read by circuits 92. Circuits 92 with thus have available updated compensation information or other information pre-stored in storage element, or circuit 90, specific to that replacement unit.

From the foregoing, it will be observed that numerous variations and modifications may be effected without departing from the spirit and scope of the invention. It is to be understood that no limitation with respect to the specific apparatus illustrated herein is intended or should be inferred. It is, of course, intended to cover by the appended claims all such modifications as fall within the scope of the claims.

The invention claimed is:

1. An assembly comprising:
a housing;
a resistive, gas responsive sensor element carried by and within the housing;
a compensator element carried by and within the housing;
a plurality of electrical connectors extending from the housing, each of the electrical connectors forming a direct electrical connection with at least one of the resistive, gas responsive sensor element and compensator element within the housing via one or more electrical traces and tracks; and
a representation of individual sensor-specific information carried, in a non-transitory computer readable medium, by and within the housing, the non-transitory computer readable medium is electrically connected within the housing in parallel with the compensator element via the plurality of electrical connectors, the representation includes at least one of sensor-specific temperature compensation information, or sensor-specific humidity compensation information to allow for individual sensor compensation and where the at least one of sensor-specific temperature compensation information, or sensor-specific humidity compensation information of the non-transitory computer readable medium is accessible by circuits external to the housing via the plurality of connectors.

2. An assembly as claim 1 where the computer readable medium includes at least one of a storage device for the compensation information, the storage device is coupled to the sensor, or, a bar coded label carried by the housing which exhibits the representation of the information.

3. An assembly as in claim 2 which includes a second resistive sensor carried by the housing.

4. An apparatus as in claim 3 where the sensors are coupled in one of, series or parallel.

5. An apparatus as in claim 4 where the device is coupled in parallel with at least one sensor and comprises a storage circuit.

6. An apparatus as in claim 5 where the housing carries a plurality of contacts external thereto with the contacts coupled to the sensors.

7. An apparatus as in claim 6 where first and second of the contacts are coupled to one sensor with, second and third contacts coupled to the other sensor.

8. An apparatus as in claim 7 where the sensors are series coupled between the first and third contacts.

9. An apparatus as in claim 8 which includes a resistive bridge circuit, external to the housing and coupled to the contacts.

10. An apparatus as in claim 8 which includes control circuits coupled to the contacts, responsive to sensor outputs that provide indicia indicative of sensed ambient gas.

11. An apparatus as in claim 10 where the control circuits include a programmable processor and associated control software.

12. A method comprising:
before assembly, detecting individual sensor-specific temperature variation characteristics of a selected resistive gas sensor;
storing a representation of the individual sensor-specific detected temperature characteristics in a non-transitory computer readable medium within a housing of the selected resistive gas sensor;
during assembly, associating the stored representation of the individual sensor-specific detected temperature characteristics with the sensor;
during assembly, providing a plurality of connectors extending into the housing, each connecting to one of a compensator element and gas sensing element of the selected resistive gas sensor and electrically connecting within the housing of the selected resistive gas sensor the non-transitory computer readable medium in parallel with the compensating element of the selected resistive gas sensor via the plurality of conductors; and
using the individual sensor-specific stored representation to temperature compensate the sensor.

13. A method as in claim 12 where storing includes storing the representation in at least one of a computer readable database, a computer readable bar code, or, a computer readable storage circuit.

14. A detector comprising:
a housing;
a socket carried by the housing;
a gas sensor which includes a gas responsive element, a compensation element, a plurality of connectors extending into the gas sensor where each of the plurality of connectors electrically connects to at least one of the gas responsive and compensator elements and associated individual sensor-specific environmental compensation information specific to the gas responsive element, the gas sensor releasably carried by the housing via operation of the plurality of connectors, the associated individual sensor-specific environmental compensation information loaded in a non-transitory computer readable medium that is also carried within by the gas sensor, the compensator element and non-transitory computer readable medium electrically connected in parallel within the gas sensor; and gas level detecting control circuits, coupled to the individual sensor-specific environmental sensor and temperature compensation information, and responsive thereto.

15. A detector as in claim 14 which includes a socket coupled to the control circuits, the sensor releasably engages the socket.

16. A detector as in claim 15 where the information is carried by the sensor in a computer readable medium.

17. A detector as in claim 16 where the computer readable medium comprises at least one of an electronic storage circuit, or a printed bar code.

18. A detector as in claim 14 where the information is selected from a class which includes at least temperature compensating information and humidity compensating information.

19. A method comprising:
providing a gas responsive detector element and compensator element;
before assembly, establishing individual sensor-specific temperature compensation information relative to that gas responsive detector element;
during assembly, coupling the individual sensor-specific information to the gas responsive detector element; and
incorporating the gas responsive detector element, the compensator element and a non-transitory computer readable medium loaded with the information into a housing of a gas detector along with a plurality of connectors extending through the housing where each of the plurality of connectors connects to at least one of the gas response detector element and compensator element and;
electrically connected the compensator element in parallel with the non-transitory computer readable medium within the housing; and
accessing the sensor-specific temperature compensation information of the non-transitory computer readable medium via the plurality of connectors.

20. A method as in claim 19 which includes, exposing the pellistor to a selected ambient atmosphere;
making a determination of an ambient gas concentration taking into account pre-stored temperature compensation information specific to that gas responsive detector element; and
generating at least one of a visually perceptible as level indicating iridicium, or an audible gas level indicating indicium.

21. A method as in claim 20 which includes, replacing the gas responsive detector element with another gas responsive detector element and associated temperature compensation information; and
making a determination of an ambient gas concentration taking into account pre-stored temperature compensation information specific to that another gas responsive detector element; and
generating at least one of a visually perceptible gas level indicating indicium, or an audible gas level indicating indicium.

* * * * *